(12) United States Patent
Dolbier, Jr. et al.

(10) Patent No.: US 9,656,989 B2
(45) Date of Patent: May 23, 2017

(54) 2-PENTAFLUOROSULFANYL (SF5) MEFLOQUINE DERIVATIVES, FORMULATIONS, METHODS OF MAKING, AND USES THEREOF

(71) Applicant: University of Florida Research Foundation, Inc., Gainesville, FL (US)

(72) Inventors: William R. Dolbier, Jr., Gainesville, FL (US); Oleksandr S. Kanishchev, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/153,139

(22) Filed: May 12, 2016

(65) Prior Publication Data

US 2016/0332988 A1   Nov. 17, 2016

Related U.S. Application Data

(60) Provisional application No. 62/160,869, filed on May 13, 2015.

(51) Int. Cl.
   *C07D 401/06*   (2006.01)

(52) U.S. Cl.
   CPC ................... *C07D 401/06* (2013.01)

(58) Field of Classification Search
   CPC .................................................... C07D 401/06
   USPC ......................................................... 514/314
   See application file for complete search history.

(56) References Cited

U.S. PATENT DOCUMENTS 7,943,787 B2   5/2011   Zheng et al.

FOREIGN PATENT DOCUMENTS

| WO | 2004011422 A1 | 2/2004 |
| WO | 2010144102 A1 | 12/2010 |
| WO | 2010144434 A1 | 12/2010 |

OTHER PUBLICATIONS

Compound CAS RN 1027193-43-6, accessible to public on Jun. 11, 2008.*
Altomonte, et al., Synthetic chemistry and biological activity of pentafluorosulphanyl (SF5) organic molecules, Journal of Fluorine Chemistry 143, Nov. 2012, 57-93.
Beier, et al., Synthesis of SF5-containing benzisoxazoles, quinolines, and quinazolines by the Davis reaction of nitro-pentafluorosulfanyl)benzenes, Beilstein Journal of Organic Chemistry 9, 2013, 411-416.
Wipf, et al., Synthesis and biological evaluation of the first pentafluorosulfanyl analogs of mefloquine, Organic and Biomolecular Chemistry 7, 2009, 4163-4165.

* cited by examiner

*Primary Examiner* — Yong Chu
(74) *Attorney, Agent, or Firm* — Thomas | Horstmeyer, LLP

(57) ABSTRACT

Provided herein are pentafluorosulfanyl ($SF_5$) mefloquine derivatives, formulations, methods of making the $SF_5$ derivatives, and uses thereof.

17 Claims, No Drawings

US 9,656,989 B2

2-PENTAFLUOROSULFANYL (SF5) MEFLOQUINE DERIVATIVES, FORMULATIONS, METHODS OF MAKING, AND USES THEREOF

CROSS-REFERENCE TO RELATED APPLICATIONS

This application claims the benefit of and priority to U.S. Provisional Patent Application No. 62/160,869, filed on May 13, 2015, entitled "2-PENTAFLUOROSULFANYL (SF5) MEFLOQUINE DERIVATIVES, FORMULATIONS, METHODS OF MAKING, AND USES THEREOF," the contents of which is incorporated by reference herein in its entirety.

BACKGROUND

Malaria is a devastating burden on the world and caused the about 627,000 deaths in 2012. Of the estimated 627,000 deaths, about 482,000 of those were children under the age of 5. While antimalarial drugs are available, the emergence of resistance to them fuels the long-felt and unmet need for improved antimalarial therapeutics.

SUMMARY

Provided herein are compounds according to Formula 1A, wherein X can be O, S, C, or N, wherein R can be H, a heterocycle side chain, a strait alkyl, a cyclic alkyl, a cyclic amine, a N substituted cyclic chain alkyl, a N substituted straight chain alkyl, or contain two substituents $R_1$ and $R_2$, wherein $R_1$ and $R_2$ is independently selected from the group of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle, wherein Z can be located in positioned in positions 6-, 7-, or 8- of Formula 1A, and wherein Z can be a perfluorinated or partially fluorinated alkyl. Z can be selected from the group of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$. In embodiments, the compound can have a formula according to Formula 1. The compounds can further contain a pharmaceutically acceptable carrier. In embodiments the compound can be an enantiomer, diastereomer, racemate, pharmaceutically acceptable salt thereof, or suitable derivative of Formula 1A.

Also provided herein are pharmaceutical compositions containing an amount of a compound according to formula 1A, wherein X can be O, S, C, or N, wherein R can be H, a heterocycle side chain, a strait alkyl, a cyclic alkyl, a cyclic amine, a N substituted cyclic chain alkyl, a N substituted straight chain alkyl, or comprise two substituents $R_1$ and $R_2$, wherein $R_1$ and $R_2$ can be independently selected from the group consisting of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle, wherein Z can be located in positioned in positions 6-, 7-, or 8- of Formula 1A, wherein Z can be a perfluorinated or partially fluorinated alkyl; and a pharmaceutically acceptable carrier. In embodiments, Z can be selected from the group consisting of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$. In embodiments, the compound can have a formula according to Formula 1. In embodiments, the amount can be an amount effective to treat or prevent infection by a protozoan of the genus Plasmodium in a subject in need thereof. In embodiments, the amount can be an amount effective to treat or prevent malaria in a subject in need thereof. In embodiment the amount can be an amount effective to treat or prevent chloroquine resistant malaria in a subject in need thereof. In embodiments, the amount can be an amount effective to treat or prevent mefloquine resistant malaria in a subject in need thereof.

Also provided herein are methods containing the step of administering an amount of a compound according to Formula 1A to a subject in need thereof, wherein X can be O, S, C, or N, wherein R is H, a heterocycle side chain, a strait alkyl, a cyclic alkyl, a cyclic amine, a N substituted cyclic chain alkyl, a N substituted straight chain alkyl, or comprise two substituents $R_1$ and $R_2$, wherein $R_1$ and $R_2$ is independently selected from the group consisting of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle, wherein Z can be located in positioned in positions 6-, 7-, or 8- of Formula 1A, wherein Z can be a perfluorinated or partially fluorinated alkyl, and wherein the subject in need thereof thereof can be infected with, suspected of being infected with, exposed to, or suspected of being exposed to a protozoan belonging to the genus Plasmodioum. In embodiments, the amount of the compound according to Formula 1A is a therapeutically effective amount. In embodiments, the protozoan is capable of causing malaria in the subject in need thereof. In embodiments, the protozoan can be resistant to chloroquine. In embodiments, the protozoan can be resistant to mefloquine. In embodiments, the amount of a compound according to Formula 1A can be contained in a pharmaceutical formulation further comprising a pharmaceutically acceptable carrier. In embodiments, Z can be selected from the group of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$. In embodiments, the compound can be according to Formula 1.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

DEFINITIONS

As used herein, "biocompatible" refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, refers to substances that have strongly polar groups that readily interact with water.

The term "hydrophobic", as used herein, refers to substances that lack an affinity for water; tending to repel and not absorb water as well as not dissolve in or mix with water.

The term "lipophilic", as used herein, refers to compounds having an affinity for lipids.

The term "amphiphilic", as used herein, refers to a molecule combining hydrophilic and lipophilic (hydrophobic) properties.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "control" or "suitable control" is an alternative subject or sample used in an experiment for comparison purposes and included to minimize or distinguish the effect of variables other than an independent variable. A "control" can be positive or negative. A "control" as used herein refers to a control that will allow determination of a response to a compound, formulation, or treatment regimen described herein. "Control" includes a level of a physiologic characteristic or other parameter in a subject to be treated before administration of a compound or formulation described herein or before a treatment regimen. "Control" includes a pre-made standard or a range of values pre-determined to represent a normal level of the paramater being measured in a subject.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to a an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "purified" is used in reference to a nucleic acid sequence, peptide, or polypeptide or other compound that has increased purity relative to the natural environment or the environment in which it was produced in.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "therapeutic" refers to treating or curing a disease or condition.

As used herein, "preventative" refers to hindering or stopping a disease or condition, such as malaria, before it occurs in a subject or while the disease or condition is still in the sub-clinical phase.

As used herein, "separated" refers to the state of being physically divided from the original source or population such that the separated compound, agent, particle, chemical compound, or molecule can no longer be considered part of the original source or population.

As used herein, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "chemotherapeutic agent" or "chemotherapeutic" refer to a therapeutic agent utilized to prevent or treat cancer.

As used herein, "dose," "unit dose," or "dosage" refers to physically discrete units suitable for use in a subject, each unit containing a predetermined quantity of the $SF_5$ containing compound, derivative thereof, or formulation thereof described herein calculated to produce the desired response or responses in association with its administration.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein "immunomodulator," refers to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A nonnaturally occurring polynucleotide, peptide, polypeptide, protein, antibody, or fragments thereof, do not require "isolation" to distinguish it from its naturally occurring counterpart.

As used herein, "variant" can refer to a polypeptide that differs from a reference polypeptide or compound, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. A typical variant of a compound can be a derivative or analogue thereof.

As used herein, "functional variant" refers to a variant of a protein, polypeptide, molecule or compound (e.g., a $SF_5$ containing molecule as described elsewhere herein) that can perform the same functions or activities as the original protein or polypeptide, although not necessarily at the same level (e.g., the variant may have enhanced, reduced, or changed functionality, so long as it retains the basic function).

As used herein, "anti-infective" refers to compounds or molecules that can either kill an infectious agent or inhibit it from spreading. Anti-infectives include, but are not limited to, antibiotics, antibacterials, antifungals, antivirals, and antiprotozoans.

As used herein, "wild-type" is the typical form of an organism, variety, strain, gene, protein, or characteristic as it occurs in nature, as distinguished from mutant forms that may result from selective breeding or transformation with a transgene.

As used herein "heterogeneous" refers to a population of molecules, including nanoparticles, proteins, and polypeptides, or a population of subunits of a molecule that contains at least 2 molecules or subunits that are different from one another.

As used herein "homogenous" refers to a population of molecules, including nanoparticles, proteins, and polypeptides, or a population of subunits of a molecule in which all the molecules or subunits are identical to one another.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "administering" refers to an administration that is oral, topical, intravenous, subcutaneous, transcutaneous, transdermal, intramuscular, intracranial, intrajoint, parenteral, intra-arteriole, intradermal, intraventricular, intracranial, intraperitoneal, intralesional, intranasal, rectal, vaginal, intraurethral, by inhalation, or via an implanted reservoir. The term "parenteral" includes subcutaneous, intravenous, intramuscular, intra-articular, intrasynovial, intrasternal, intrathecal, intrahepatic, intralesional, and intracranial injections or infusion techniques.

As used herein, "composition" refers to a combination of an active agent(s) and another compound or composition, inert (for example, a detectable agent or label) or active, such as an adjuvant.

As used herein, "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, C1-C6 alkyl, C2-C6 alkenyl, C1-C6 haloalkyl, C1-C6 alkoxy, C1-C6 haloalkoxy, C2-C6 alkynyl, C3-C8 cycloalkenyl, (C3-C8 cycloalkyl)C1-C6 alkyl, (C3-C8 cycloalkyl)C2-C6 alkenyl, (C3-C8 cycloalkyl) C1-C6 alkoxy, C3-C7 heterocycloalkyl, (C3-C7 heterocycloalkyl)C1-C6 alkyl, (C3-C7 heterocycloalkyl)C2-C6 alkenyl, (C3-C7 heterocycloalkyl)C1-C6 alkoxyl, hydroxy, carboxy, oxo, sulfanyl, C1-C6 alkylsulfanyl, aryl, heteroaryl, aryloxy, heteroaryloxy, aralkyl, heteroaralkyl, aralkoxy, heteroaralkoxy, nitro, cyano, amino, C1-C6 alkylamino, di-(C1-C6 alkyl) amino, carbamoyl, (C1-C6 alkyl)carbonyl, (C1-C6 alkoxy) carbonyl, (C1-C6 alkyl)aminocarbonyl, di-(C1-C6 alkyl) aminocarbonyl, arylcarbonyl, aryloxycarbonyl, (C1-C6 alkyl)sulfonyl, and arylsulfonyl. The groups listed above as suitable substituents are as defined hereinafter except that a suitable substituent may not be further optionally substituted.

As used herein, "optionally substituted" indicates that a group may be unsubstituted or substituted with one or more substituents as defined herein.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, and $C_3$-$C_{30}$ for branched chains). In other embodiments, a straight chain or branched chain alkyl contains 20 or fewer, 15 or fewer, or 10 or fewer carbon atoms in its backbone. Likewise, in some embodiments cycloalkyls have 3-10 carbon atoms in their ring structure. In some of these embodiments, the cycloalkyl have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O— alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

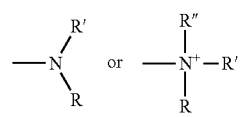

wherein R, R', and R" each independently represent a hydrogen, an alkyl, an alkenyl, —(CH$_2$)$_m$—R$_c$ or R and R' taken together with the N atom to which they are attached complete a heterocycle having from 4 to 8 atoms in the ring structure; R$_c$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

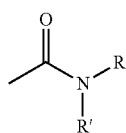

wherein R and R' are as defined above.

As used herein, "Aryl" refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2, 5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

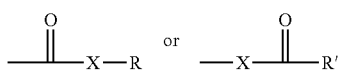

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium.

As used herein, the term "nitro" refers to $-NO_2$; the term "halogen" designates $-F$, $-Cl$, $-Br$, or $-I$; the term "sulfhydryl" refers to $-SH$; the term "hydroxyl" refers to $-OH$; and the term "sulfonyl" refers to $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "therapeutically effective amount" refers to the amount of a $SF_5$ containing compound described herein, derivative thereof, pharmaceutical formulation thereof, auxiliary agent, or secondary agent described herein that will elicit the biological or medical response of a tissue, system, animal, or human that is being sought by the researcher, veterinarian, medical doctor or other clinician. "Therapeutically effective amount" includes that amount of $SF_5$ containing antimalarial compound(s), derivative(s) thereof, or pharmaceutical formulation(s) thereof that, when administered alone or co-administered with a secondary agent, is sufficient to prevent development of, reduce or alleviate to some extent, one or more of the symptoms of an infection with a protozoan belonging to the genus of Plasmodium. "Therapeutically effect amount" includes that amount of a $SF_5$ containing antimalarial compound(s), derivative thereof, or pharmaceutical formulation thereof that, when administered alone or co-administered with a secondary agent, that is sufficient to treat or prevent infection with a protozoan that is resistant to chloroquine, mefloquine, or combinations thereof. Those of ordinary skill in the art will appreciate that the therapeutically effective amount will vary depending on the exact chemical structure of the $SF_5$ containing antimalarial compound(s), derivative thereof, or pharmaceutical formulations thereof, the exact protozoan or other malaria causative agent, the severity and/or type of the infection or other disease, disorder, syndrome, or symptom thereof being treated, the route of administration, the time of administration, the rate of excretion, the drug combination, the judgment of the treating physician, the dosage form, and the age, weight, general health, sex and/or diet of the subject to be treated.

As used herein, "treat," "treating," "treatment" and grammatical variations thereof as used herein include partially or completely delaying, alleviating, mitigating or reducing the intensity of one or more attendant symptoms of a disorder or condition such as malaria and/or alleviating, mitigating or impeding one or more causes of a disorder or condition such as malaria. Treatments according to the embodiments disclosed herein may be applied preventively, prophylactically, palliatively or remedially. In some instances, the terms "treat," "treating," "treatment" and grammatical variations thereof include partially or completely reducing a condition or symptom associated with, for example, malaria as compared with prior to treatment of the subject or as compared with the incidence of such condition or symptom in a general or study population.

As used herein, "functional analogue" refers to a compound molecule, nucleotide sequence, protein, and the like, that has the same or similar physical, chemical, biochemical, pharmacological properties, or elicit the same effect as another molecule, protein, and the like. In some embodiments, functional analogues are also structural analogues. In other embodiments, functional analogues are not structural analogues.

As used herein, "analogue" refers to both the terms "structural analogue" and "functional analogue."

As used herein, "heterologue" refers to compounds, molecules, nucleotide sequences (including genes), and polypeptide sequences (including peptides and proteins) that are different in both activity (function) and sequence or chemical structure.

As used herein, "homologue" refers to a polypeptide sequence that shares a threshold level of similarity and/or identity as determined by alignment of matching amino acids. Two or more polypeptides determined to be homologues are said to be homologues. Homology is a qualitative term that describes the relationship between polypeptide sequences that is based upon the quantitative similarity.

As used herein, "paralog" refers to a homologue produced via gene duplication of a gene. In other words, paralogs are homologues that result from divergent evolution from a common ancestral gene.

As used herein, "orthologs" refers to homologues produced by speciation followed by divergence of sequence but not activity in separate species. When speciation follows duplication and one homologue sorts with one species and the other copy sorts with the other species, subsequent divergence of the duplicated sequence is associated with one or the other species. Such species specific homologues are referred to herein as orthologs.

As used herein, "xenologs" are homologues resulting from horizontal gene transfer.

Discussion

Malaria is a mosquito-borne infections disease of humans and other animals caused by parasitic protozoans belonging to the genus *Plasmodium*. Malaria causes symptoms that typically include fever, fatigue, vomiting, and headaches. In severe cases, it can cause yellow skin, seizures, coma, and death. Mefloquine is an orally-administered antimalarial drug effective for prophylaxis and for acute therapeutic treatment of malaria. Mefloquine is currently strictly used for chloroquine-resistant strains of malaria. However, its potential is limited due to its adverse central nervous system (CNS) effects, which include anxiety, depression, hallucinations and seizures. Despite the relatively high incidence of side effects, mefloquine continues to be used due to its long half-life, relative safety in pregnancy, activity against resistant strains, and the absence of effective alternatives. Mefloquine can only be taken for up to 6 months due to those side effects and subsequently, alternative drugs need to be taken.

Until recently, melfoquine was the drug of choice for U.S. Army soldiers in regions where malaria is endemic, primarily because of its long half-life, which allows weekly administration. However, associations of mefloquine with adverse neuropsychiatric effects, namely anxiety disorders, hallucinations, sleep disturbances and delirium, have curtailed its use. Those effects are connected with the ability of mefloquine to cross blood-brain barrier, accumulate and interact with several CNS targets. Nevertheless, mefloquine is still the only weekly-administered drug that is efficient against chloroquine-resistant *P. falciparum* malaria parasites; therefore, mefloquine has an important place in malaria treatment.

In addition to the adverse side effects, the protozoans causing malaria in some regions have developed a resistance to mefloquine. This has led to the emergence of multi-drug resistant strains of malaria. In view of the adverse side effects and emerging resistance, there exists a need for improved antimalarial drugs.

With the aforementioned shortcomings in mind, described herein are pentafluorosulfanyl ($SF_5$) mefloquine derivatives, formulations, methods of making the $SF_5$ derivatives, and uses thereof. The $SF_5$ mefloquine derivatives described herein can contain a $SF_5$ group substituted in the 2 position on the quinoline of mefloquine. The $SF_5$ mefloquine derivatives described herein can be used to treat and/or prevent infection and/or disease caused by a protozoan of the genus *Plasmodium*. The $SF_5$ mefloquine derivatives described herein can be used to treat and/or prevent malaria. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

$SF_5$ Containing Antimalarial Compounds and Formulations Thereof $SF_5$ Containing Antimalarial Compounds Mefloquine includes two trifluoromethyl groups: one at position 2 (in the benzene portion of the quinoline) and one at position 8 (in the pyridine of the quinoline) of the quinoline moiety. Current $SF_5$ modifications to mefloquine are limited to mefloquine compound having a $SF_5$ group in position 6, 7, or 8 of the quinoline group. In contrast, the compounds described herein can have a $SF_5$ group in the 2 position of the quinoline group. Thus, in the compounds described herein, $SF_5$ can replace the trifluoromethyl group at position 2. The substitution of the trifluoromethyl group at position 2 with an $SF_5$ group can have an increased efficacy against at least malaria as compared with unmodified mefloquine.

The $SF_5$ compound can contain quinoline and can have a formula according to Formula 1. The $SF_5$ compound can can be an enantiomer, diastereomer, racemate, or pharmaceutically acceptable salt of the compound according to Formula 1.

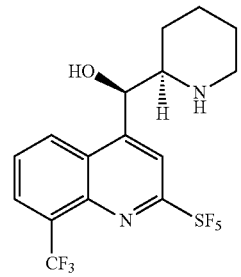

Formula 1

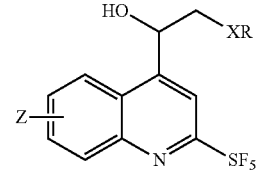

Formula 1A

In some embodiments, the compound can be a suitable derivative of Formula 1. Suitable derivatives can be derivatives of Formula 1 that can treat or prevent malaria in a subject. In some embodiments, the piperidine moiety can be substituted with other suitable groups to provide derivatives represented by Formula 1A, wherein X is an oxygen atom, a sulfur atom, a carbon atom or a nitrogen atom. R is a hydrogen atom, a side chain containing heterocycle, a straight chain alkyl group, a cyclic alkyl group, a straight chain alkyl group containing a nitrogen atom, a cyclic amine, a cyclic chain alkyl group containing one or more heteroatoms, an aryl group, or a straight chain alkyl group containing one or more heteroatoms. In further embodiments, R can represent two substituents, $R_1$ and $R_2$. $R_1$ can be a hydrogen atom, a side chain containing heterocycle, a straight chain alkyl group, a cyclic alkyl group, a straight chain alkyl group containing a nitrogen atom, a cyclic alkyl group containing a nitrogen atom, a cyclic amine, an imidazole, or a triazole. $R_2$ can be a hydrogen atom, a straight chain group, a cyclic alkyl group, a straight chain alkyl group containing a nitrogen atom, a cyclic alkyl group containing a nitrogen atom, a cyclic amine, an imidazole, or a triazole. In some embodiments, $R_1$ and $R_2$ can be the same. In other embodiments, $R_1$ and $R_2$ can be different from each other. In some embodiments, $R_1$ and $R_2$ can be joined to each other to form a cyclic amine, aryl group, or heterocycle. Substituent Z can be located in positions 6-, 7- or 8- of 2-$SF_5$ substituted quinoline core and can be represented by $CF_3$, $SF_5$, $SCF_3$, $HCF_2$, $ClCF_2$, $BrCF_2$, $ICF_2$, $HCF_2S$, $C_2F_5$, $CF_2CF_2H$, $CF_2SF_5$ or other perfluorinated or partially fluorinated small alkyl (alkenyl) chain.

Pharmaceutical Formulations

The $SF_5$ containing antimalarial compounds described herein can be provided to a subject alone or as an ingredient, such as an active ingredient, in a pharmaceutical formulation. As such, also described herein are pharmaceutical formulations containing one or more of the $SF_5$ containing antimalarial compounds described herein. In some embodiments, the pharmaceutical formulations contain a therapeutically effective amount of one or more $SF_5$ containing antimalarial compounds described herein. In other embodiments, the $SF_5$ containing antimalarial compounds described herein can be used in the manufacture of a medicament for the treatment or prevention of an infection or symptom thereof caused by a protozoan causing malaria in a subject.

The pharmaceutical formulations described herein can be administered to a subject in need thereof. In some embodiments, the subject in need thereof can be infected with or suspected of being infected with a protozoan belonging to the genus *Plasmodium*. In some embodiments, the protozoan can cause malaria. The protozoan can be *P. falciparum*. The protozoan causing malaria can be resistant to chloroquine, mefloquine, or combinations thereof.

Pharmaceutically Acceptable Carriers and Auxiliary Ingredients and Agents

The pharmaceutical formulations containing an amount or therapeutically effective amount of the $SF_5$ containing antimalarial compound(s) described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the amount or therapeutically effective amount of the $SF_5$ containing antimalarial compound(s), the pharmaceutical formulation can also include a therapeutically effective amount of auxiliary active agents, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ϵ, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veraliride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravidemtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Effective Amounts of the $SF_5$ Containing Antimalarial Compound and Auxiliary Agents The pharmaceutical formulations can contain a therapeutically effective amount of an $SF_5$ containing antimalarial compound(s) and/or a therapeutically effective amount of an auxiliary agent. In some embodiments, the therapeutically effective amount of the $SF_5$ containing antimalarial compound(s) can range from about 0.01 mg/kg to about 20 mg/kg. In some embodiments, the therapeutically effective mount of the $SF_5$ containing antimalarial compound(s) can range from about 1 mg/kg to about 10 mg/kg.

In embodiments where there is an auxiliary active agent contained in the pharmaceutical formulation in addition to the $SF_5$ containing antimalarial compound(s), the therapeutically effective amount of the auxiliary active agent will vary depending on the auxiliary active agent. In some embodiments, the effective amount of the auxiliary active agent ranges from 0.001 micrograms to about 1 milligrams. In other embodiments, the effective amount of the auxiliary active agent ranges from about 0.01 IU to about 1000 IU. In further embodiments, the effective amount of the auxiliary active agent ranges from 0.001 mL to about 1 mL. In yet other embodiments, the effective amount of the auxiliary active agent ranges from about 1% w/w to about 50% w/w of the total pharmaceutical formulation. In additional embodiments, the effective amount of the auxiliary active agent ranges from about 1% v/v to about 50% v/v of the total pharmaceutical formulation. In still other embodiments, the effective amount of the auxiliary active agent ranges from about 1% w/v to about 50% w/v of the total pharmaceutical formulation.

The auxiliary active agent can be included in the pharmaceutical formulation or can exist as a stand-alone compound or pharmaceutical formulation that is administered contemporaneously or sequentially with the conjugate compound, derivative thereof or pharmaceutical formulation thereof. In embodiments where the auxiliary active agent is a stand-alone compound or pharmaceutical formulation, the therapeutically effective amount of the auxiliary active agent can vary depending on the auxiliary active agent used. In some of these embodiments, the therapeutically effective amount of the auxiliary active agent can range from 0.001 micrograms to about 1000 grams. In other embodiments, the therapeutically effective amount of the auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the auxiliary active agent can range from about 1% w/w to about 50% w/w of the total auxiliary active agent pharmaceutical formulation. In additional embodiments, the therapeutically effective amount of the auxiliary active agent can range from about 1% v/v to about 50% v/v of the total pharmaceutical formulation. In still other embodiments, the therapeutically effective amount of the auxiliary active agent can range from about 1% w/v to about 50% w/v of the total auxiliary agent pharmaceutical formulation.

Dosage Forms

In some embodiments, the pharmaceutical formulations described herein may be in a dosage form. The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, intraurethral, parenteral, intracranial, subcutaneous, intramuscular, intravenous, and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. In some embodiments, the oral dosage form can contain about 100 mg, about 200 mg, or about 300 mg of a pharmaceutical formulation containing a therapeutically effective amount or an appropriate fraction thereof of the $SF_5$ containing antimalarial compound(s). The oral dosage form can be administered to a subject in need thereof. In some embodiments, this is a subject infected with or suspected of being infected with a protozoan causing malaria.

Where appropriate, the dosage forms described herein can be microencapsulated. The dosage form can also be prepared to prolong or sustain the release of any ingredient. In some embodiments, the $SF_5$ containing antimalarial compound(s). is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the the $SF_5$ containing antimalarial compound(s), auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the $SF_5$ containing antimalarial compound(s), derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the $SF_5$ containing antimalarial compound(s), auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a conjugate compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, 8 or more times daily, in which 1, 2, 3 more more doses are delivered each time.

For some dosage forms suitable and/or adapted for inhaled administration, the pharmaceutical formulation is a dry powder inhalable formulations. In addition to the the the $SF_5$ containing antimalarial compound(s), auxiliary active ingredient, and/or pharmaceutically acceptable salt thereof, such a dosage form can contain a powder base such as lactose, glucose, trehalose, manitol, and/or starch. In some of these embodiments, the conjugate compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for injection can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of an the $SF_5$ containing antimalarial compound(s) per unit dose. In an embodiment, the predetermined amount of the $SF_5$ containing antimalarial compound(s) is a therapeutically effective amount of the $SF_5$ containing antimalarial compound(s) to treat, prevent, or mitigate the symptoms of an infection with a malaria-causing protozoan. In other embodiments, the predetermined amount of the $SF_5$ containing antimalarial compound(s) is an appropriate fraction of the effective amount of the active ingredient. Such unit doses may therefore be administered once or more than once a day. Such pharmaceutical formulations may be prepared by any of the methods well known in the art.

Methods of Making the $SF_5$ Containing Antimalarial Compound(s)

The $SF_5$ containing antimalarial compounds described herein can be synthesized by any method known to those skilled in the art of synthetic chemistry and according to the synthesis scheme(s) described herein. In some embodiments, the $SF_5$ containing antimalarial compound(s) described herein can be synthesized according to Scheme 1.

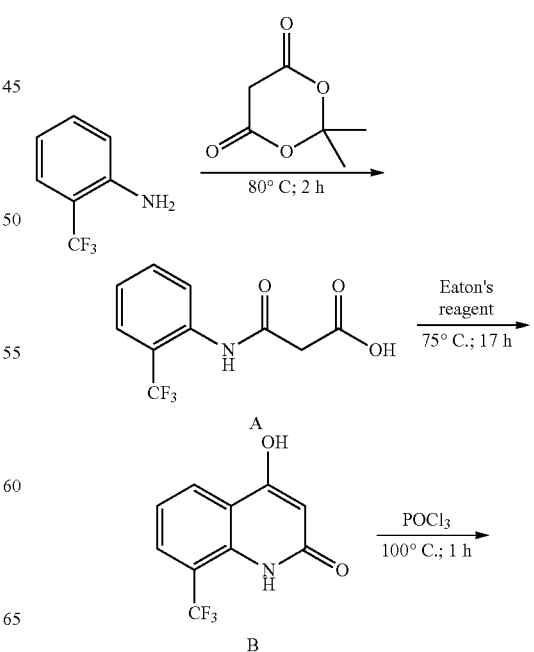

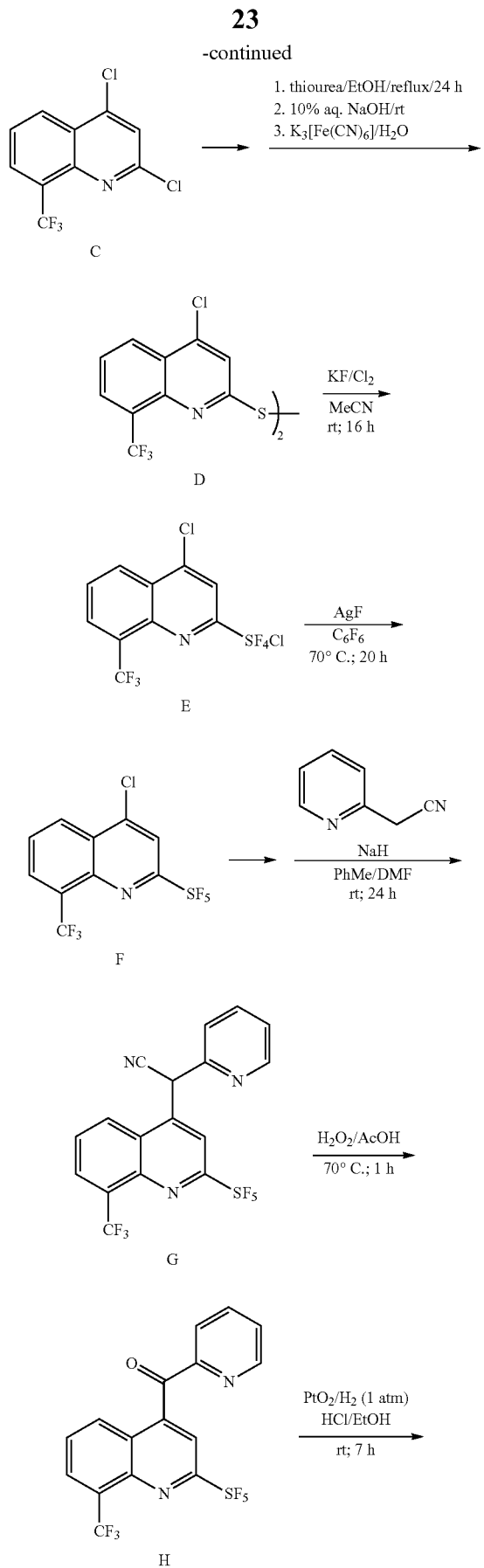

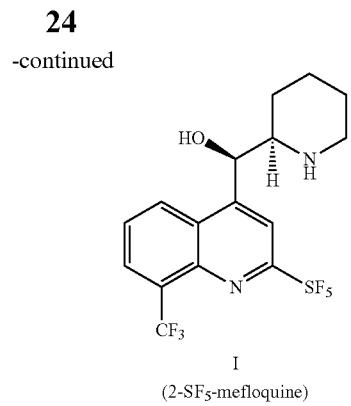

I
(2-SF₅-mefloquine)

Suitable variations of Scheme 1 will be appreciated by those of ordinary skill in the art to substitute a CF₃ group in the starting 2-trifluoromethyl aniline with any other substituent in ortho-, meta- or para-position of aniline to produce correspondingly substituted intermediate A and further corresponding quinoline intermediates B, C, D, F with any substituent in position 6-, 7- or 8. One or more steps or combination of steps demonstrated in Scheme 1 can be used to synthesis heterocycles with an SF₅ group in the alpha position to the heteroatom.

Methods of Using the SF₅ Containing Antimalarial Compound(s) and Formulations Thereof The SF₅ containing antimalarial compound(s) and pharmaceutical formulations thereof described herein can be used for treatment or prevention of a disease, disorder, syndrome, or a symptom thereof. In some embodiments, the SF₅ containing compound(s) described herein can be used to treat a subject infected with or suspected of being infected with a protozoan that causes malaria. In some embodiments, the SF₅ containing antimalarial compound(s) and pharmaceutical formulations thereof described herein can be used for treatment or prevention of infection with a protozoan belonging to the genus *Plasmodium*. In some embodiments, the protozoan *P. falciparum*. In some embodiments, the protozoan causing malaria can be resistant to chloroquine, mefloquine, or combinations thereof.

In some embodiments, the amount administered can be the therapeutically effective amount of the SF₅ containing antimalarial compound(s) or pharmaceutical formulations thereof. For example, the SF5 containing antimalarial compound(s) or pharmaceutical formulations thereof can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6 or more. In further embodiments, the compounds, formulations, or salts thereof are administered one or more times per week, such as 1, 2, 3, 4, 5, 6 or more times per week. In other embodiments, the SF₅ containing antimalarial compound(s) or pharmaceutical formulations thereof are administered one or more times per month, such as 1 to 5 or more times per month. In still further embodiments, the SF₅ containing antimalarial compound(s) or pharmaceutical formulations thereof are administered one or more times per year, such as 1 to 11 or more times per year.

The SF₅ containing antimalarial compound(s) or pharmaceutical formulations thereof can be co-administered with a secondary agent by any convenient route. The secondary agent is a separate compound and/or formulation from the SF$_5$ containing antimalarial compound(s) or pharmaceutical formulation thereof. The secondary agent can be administered simultaneously with the SF$_5$ containing antimalarial compound(s) or pharmaceutical formulation thereof or sequentially with the SF$_5$ containing antimalarial compound(s) or pharmaceutical formulation thereof. The secondary agent can have an additive or synergistic effect to the SF$_5$ containing antimalarial compound(s) or pharmaceutical formulation thereof. Suitable secondary agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, H$_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H$_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravidemtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase Erwinia chrysanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

In embodiments where the $SF_5$ containing antimalarial compound(s) or pharmaceutical formulation thereof is simultaneously co-administered with a secondary agent, the $SF_5$ containing antimalarial compound or pharmaceutical formulation thereof is administered to the subject at substantially the same time as the secondary agent. As used in this context "substantially the same time" refers to administration of the $SF_5$ containing antimalarial compound(s) or pharmaceutical formulation thereof and a secondary agent where the period of time between administration of the $SF_5$ containing antimalarial compound(s) or pharmaceutical formulation thereof and a secondary agent is between 0 and 10 minutes.

In embodiments where the $SF_5$ containing antimalarial compound(s) or pharmaceutical formulation thereof are sequentially co-administered with a secondary agent, the $SF_5$ containing antimalarial compound(s) or pharmaceutical formulation thereof can be administered first followed by administration of the secondary agent after a period of time. In other embodiments where the $SF_5$ containing antimalarial compound(s) or pharmaceutical formulation thereof are sequentially co-administered with a secondary agent, the secondary agent can be administered first followed by administration of the $SF_5$ containing antimalarial compound(s) or pharmaceutical formulation thereof after a period of time. In any embodiment, the period of time can range from 10 minutes to about 96 or more hours. In some embodiments the period of time can be about 10 minutes, about 30 minutes, about 1 hour, about 2 hours, about 4 hours, about 6 hours, about 8 hours, about 10 hours, or about 12 or more hours. The sequential administration can be repeated as necessary over the course of the period of treatment.

The amount of the $SF_5$ containing antimalarial compound(s), pharmaceuticals formulations thereof, and secondary agents described herein can be administered in an amount ranging from about 0.01 mg to about 10 g or more per day, as calculated as the free or unsalted compounds or pharmaceutical formulations. The amount of $SF_5$ containing antimalarial compound(s), pharmaceuticals formulations thereof, and secondary agents described herein can be administered in an amount ranging from about 0.01 µM to about 10 µM or more per day.

Kits Containing the $SF_5$ Containing Compounds and Formulations Thereof

The $SF_5$ containing antimalarial compound(s) and pharmaceuticals formulations thereof described herein can be presented as a combination kit. As used herein, the terms "combination kit" or "kit of parts" refers to the $SF_5$ containing antimalarial compound(s) or pharmaceuticals formulations thereof described herein and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

The combination kit can contain each agent, compound, pharmaceutical formulation or component thereof, in separate compositions or pharmaceutical formulations. The separate compositions or pharmaceutical formulations can be contained in a single package or in separate packages within the kit. Also provided in some embodiments, are buffers, diluents, solubilization reagents, cell culture media and other reagents. These additional components can be contained in a single package or in separate packages within the kit.

In some embodiments, the combination kit also includes instructions printed on or otherwise contained in a tangible medium of expression. The instructions can provide information regarding the content of the $SF_5$ containing antimalarial compound(s) or pharmaceuticals formulations thereof, pharmaceutical formulations thereof, and/or other auxiliary agent contained therein, safety information regarding the content of the $SF_5$ containing antimalarial compound(s), pharmaceuticals formulations thereof, pharmaceutical formulations thereof, auxiliary agent, or secondary contained therein, information regarding the dosages, indications for use, and/or recommended treatment regimen(s) for the $SF_5$ containing antimalarial compound(s), pharmaceutical formulations thereof, and/or other auxiliary or secondary agent contained therein. In some embodiments, the instructions provide directions for administering the compounds, pharmaceutical formulations, or salts thereof to a subject infected with or suspected of being infected with a protozoan. In some embodiments, the protozoan causes malaria. In some embodiments, the protozoan can belong to the genus *Plasmodium*. In other embodiments, he protozoan can be *P. falciparum*. The protozoan causing malaria can be resistant to chloroquine, mefloquine, or combinations thereof.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Intermediate A of Scheme 1

Intermediate compound A of Scheme 1 has a formula according to Formula 2.

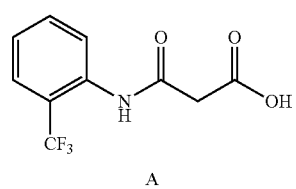

Formula 2

A

The compound of Formula 2 was made by mixing 2-Trifluoromethylaniline (10.0 g; 62 mmol) and 2,2-dimethyl-1,3-dioxane-4,6-dione (Meldrum's acid; 17.9 g; 124 mmol) together and heating the mixture with stirring at about 90° C. for about 2 h. After cooling, a solid was obtained and recrystallized from chloroform to give Intermediate A (Formula 2), which was a white solid (9.4 g; 61% yield). $^1$H NMR (CDCl$_3$): δ 3.42 (s, 2H); 7.17 (t, 1H); 7.48 (t, 1H); 7.55 (d, 1H); 8.08 (d, 1H); 9.95 (br, 1H). $^{19}$F NMR (CDCl$_3$): δ −61.6 (s).

Example 2

Intermediate Compound B of Scheme 1

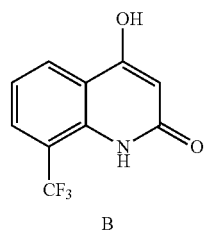

Formula 3

B

Intermediate compound B (Formula 3) was made by mixing intermediate compound A (Formula 2) (10.0 g; 40 mmol) and Eaton's reagent (100 mL) and heated with stirring at about 70° C. for about 20 h. After cooling, the reaction mixture was poured on ice. The solid precipitate was filtered, washed with water, and dried to give intermediate compound B (Formula 3), which was a white solid (5.6 g; 60% yield). $^1$H NMR (CDCl$_3$): δ 6.05 (s, 1H); 7.19 (t, 1H); 7.71 (d, 1H); 8.11 (d, 1H). $^{19}$F NMR (CDCl$_3$): δ −61.0 (s).

Example 3

Intermediate Compound C of Scheme 1

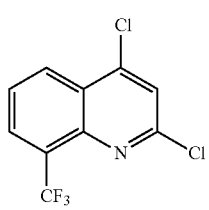

Formula 4

C

Intermediate compound C (Formula 4) was made by mixing compound B (Formula 2) (5.5 g; 24 mmol) and POCl$_3$ (40 mL) and heating the mixture with stirring at about 100° C. for about 1 h. After cooling, the reaction mixture was poured on ice. Solid precipitate was filtered, washed with water, and dried to give intermediate compound C (Formula 4), which was a light brown solid (4.85 g; 76% yield). $^1$H NMR (CDCl$_3$): δ 7.61 (s, 1H); 7.71 (t, 1H); 8.15 (d, 1H); 8.42 (d, 1H). $^{19}$F NMR (CDCl$_3$): δ −60.8 (s).

Example 4

Intermediate Compound D of Scheme 1

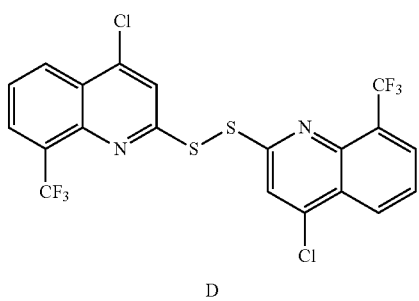

Formula 5

D

Intermediate compound D (Formula 5) was made by mixing Intermediate compound C (6.4 g; 24 mmol) and thiourea (1.83 g; 24 mmol) in EtOH (125 mL) and heating the mixture with stirring at reflux for about 20 h. the solvent was evaporated in vacuo and 10% aq. NaOH solution (250 mL) was added to the residue. After stirring at ambient for about 24 h, a solution of $K_3[Fe(CN)_6]$ (7.9 g) in water (100 mL), was added to it and stirring at ambient temperature was continued for about 24 h. The precipitate was filtered, washed with water, and dried. Further, purification by column chromatography provided pure compound D (Formula 5), which was a colorless solid (1.26 g; 20% yield). $^1$H NMR (300 MHz, CDCl3): δ 7.59 (t, $^1$H); 7.87 (s, $^1$H); 8.03 (d, $^1$H); 8.37 (d, $^1$H). $^{19}$F NMR (125 MHz, CDCl$_3$): δ −61.1 (s). HRMS (+ESI/DART): m/z calcd. for $[C_{20}H_9Cl_2F_6N_2S_2]$+: 524.9483. found: 524.9464.

Example 5

Intermediate Compound E of Scheme 1

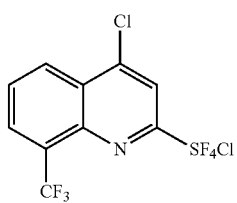

Formula 6

E

Intermediate compound E (Formula 6) was made by preparing an oven dried 30 mL narrow mouth FEP Nalgene® bottle and equipping it with a magnetic stir bar. The FEP Nalgene® bottle was charged with an anhydrous spray-dried (0.72 g; 12.4 mmol) and anhydrous MeCN (10 mL) under argon atmosphere. The charged FEP Nalgene® bottle was cooled in a n ice/water bath while chlorine gas was bubbled through the stirred reaction mixture until visible saturation was achieved. The FEP Nalgene® bottle was resealed with closure and weighed. The gain in weight was equal to the amount of chlorine introduced into the reaction (0.5 g; 5 mmol). At that point, intermediate compound D (Formula 5) (0.4 g; 0.75 mmol) was added in one portion, and the reaction mixture was stirred with cooling in an ice/water bath for 2 h and then at room temperature for 20 h. The reaction mixture was filtered under dry nitrogen pressure and the filter cake was washed with anhydrous MeCN (10 mL). The filtrate was evaporated in vacuo to give crude intermediate compound E (Formula 6). $^{19}$F NMR (125 MHz, CDCl$_3$): δ −59.8 (s, 3F, CF$_3$); +123.7 (s, 4F, SF$_4$Cl).

Example 6

Intermediate Compound F of Scheme 1

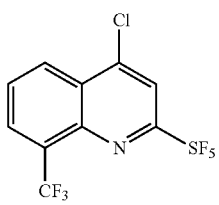

Formula 7

F

Intermediate compound F (Formula 7) was prepared by dissolving crude Intermediate compound F (Formula 6) in hexafluorobenzene (1.5 mL) was placed under argon atmosphere into a pre-weighed flat-bottomed 7 mL PFA vial with a PFA closure. Solid AgF (0.4 g; 3 mmol) was then added in one. The vial was sealed with closure and placed onto a hot plate that was preheated to 70° C., and then left for about 20 h until full consumption of the starting material was observed by $^{19}$F NMR. The content of the vial was then washed out into a beaker first with CH$_2$Cl$_2$ (30 mL) and then with water (30 mL), the contents of the beaker stirred for 1 h and then filtered from solids. The organic phase was separated and the aqueous phase extracted with CH$_2$Cl$_2$ (20 mL). The combined CH$_2$Cl$_2$ extracts were dried with MgSO$_4$. The residue obtained after filtration and evaporation of solvent in vacuo was purified by column chromatography, eluting with hexane to give the intermediate compound F (Formula 7), which was a colorless solid. $R_F$=0.45 (PE-CH$_2$Cl$_2$ 9:1). $^1$H NMR (300 MHz, CDCl$_3$): δ 7.87 (t, 1H); 8.00 (s, 1H); 8.26 (d, 1H); 8.52 (d, 1H). $^{19}$F NMR (125 MHz, CDCl$_3$): δ −61.2 (s, 3F, CF$_3$); 51.4 (d, 4F, SF$_5$); 75.3 (p, 1F, SF$_5$). HRMS (+ESI/DART): m/z calcd. for $[C_{10}H_5ClF_8NS]^+$: 357.9703. found: 357.9712.

Example 7

Intermediate Compound G of Scheme 1

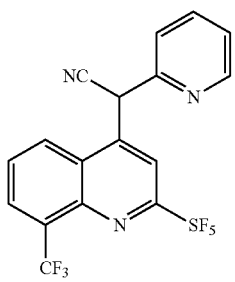

Formula 8

G

Intermediate compound G (Formula 8) was made by first adding 2-pyridineacetonitrile (18 mg; 0.15 mmol) to a suspension of of NaH (6 mg; 0.15 mmol) in toluene/DMF mixture (2:1; 1 mL). After stirring at ambient temperature for about 30 min, a solution of intermediate compound F (Formula 7) (25 mg; 0.07 mmol) in toluene/DMF mixture (2:1; 1 mL) was added and the reaction mixture was stirred at about 20 h. The reaction mixture was then diluted with ethylacetate (15 mL) and water (15 mL). The organic phase was separated, washed with water (3×10 mL), dried (MgSO$_4$) and concentrated. The residue was purified by column chromatography eluting with EtOAc/PE (50:50) to provide intermediate compound G (Formula 8), which was a dark orange solid (25 mg; 83% yield). $R_F$=0.45 (PE-EA 1:1). $^1$H NMR (300 MHz, CDCl$_3$): δ 6.05 (s, 1H); 7.32 (dd, 1H); 7.47 (d, 1H); 7.79 (m, 2H); 8.13 (s, 1H); 8.21 (d, 1H); 8.44 (d, 1H); 8.60 (d, 1H). $^{19}$F NMR (125 MHz, CDCl$_3$): δ −61.2 (s, 3F, CF$_3$); 51.2 (d, 4F, SF$_5$); 75.5 (p, 1F, SF$_5$).

Example 8

Intermediate Compound H of Scheme 1

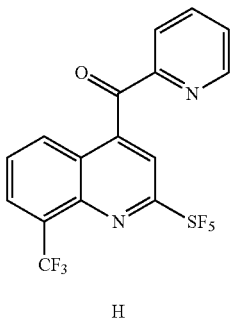

Formula 9

H

Intermediate compound H (Formula 9) was made by first adding 30% aq. H$_2$O$_2$ (60 mg; 0.6 mmol) to a solution of Intermediate compound G (Formula 9) in AcOH (1 mL). After cooling the reaction mixture was diluted with water and the precipitated crude product was filtered, washed with water, and dried to give intermediate compound H (Formula 9), which was a colorless solid (20 mg; 85% yield). $^1$H NMR (300 MHz, CDCl$_3$): 7.60 (m, 1H); 7.73 (t, 1H); 7.99 (s, 1H); 8.03 (m, 1H); 8.13 (d, 1H); 8.22 (d, 1H); 8.38 (d, 1H); 8.63 (dm, 1H). $^{19}$F NMR (125 MHz, CDCl$_3$): δ −61.3 (s, 3F, CF$_3$); 51.1 (d, 4F, SF$_5$); 75.8 (p, 1F, SF$_5$).

Example 9

2-SF5 Substituted Quinoline Compound

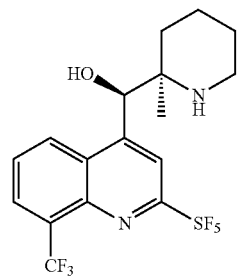

Formula 1

I

An SF5 substituted quinoline compound according to Formula 1 (Compound I of Scheme 1) was made by first adding concentrated HCl (24 mg) followed by PtO$_2$ (4 mg; 0.018 mmol) to a solution of intermediate compound H (Formula 9) in ethanol (2 mL). The system was then flushed with hydrogen and then hydrogenated under balloon pressure of hydrogen at ambient temperature for about 7 h. The reaction mixture was then filtered, basified with 25% NH$_4$OH and then evaporated to dryness. The solid residue was treated with DCM, filtered and evaporated. The crude product was purified by column chromatography eluted with DCM/MeOH (9:1) to give an SF5 substituted quinoline compound (Formula 1) (2-SF$_5$-mefloquine) as a mixture of diastereoisomers ((dr ~20:1)—10 mg (50% yield). $R_F$=0.4 (DCM-MeOH 9:1). $^1$H NMR (300 MHz, acetone-d$_6$): δ 8.78 (d, 1H); 8.25 (s, 1H); 7.99 (d, 1H); 7.34 (t, 1H); 6.48 (s, 1H); 3.71 (d, 1H); 3.59 (d, 1H); 3.20 (dt, 1H); 1.91 (m, 2H); 1.78 (d, 1H); 1.37 (m, 1H); 1.30 (m, 2H). $^{19}$F NMR (125 MHz, acetone-d$_6$): δ −60.1 (s, 3F, CF$_3$); 51.7 (d, 4F, SF$_5$); 78.1 (p, 1F, SF$_5$).

We claim:
1. A compound according to Formula 1A

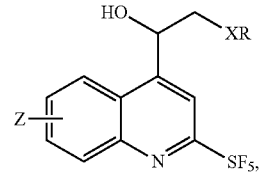

Formula 1A wherein X is O, S, —CR'R", NR',
wherein R is H, a heterocycle side chain, a straight alkyl, a cyclic alkyl, a cyclic amine, a N substituted cyclic alkyl, or a N substituted straight chain alkyl,
wherein R' and R" are each independently selected from the group consisting of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle,
wherein Z is located in positioned in positions 6-, 7-, or 8- of Formula 1A, and
wherein Z is a perfluorinated or partially fluorinated alkyl.

2. The compound of claim 1, wherein in Z is selected from the group consisting of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$.

3. The compound of claim 1, wherein the compound has a formula according to Formula 1

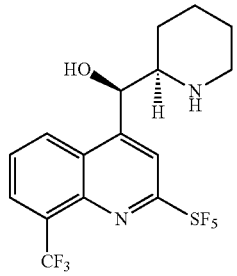

Formula 1

4. The compound of claim 1, further comprising a pharmaceutically acceptable carrier.

5. The compound of claim 1, wherein the compound is an enantiomer, diastereomer, racemate, or a pharmaceutically acceptable salt thereof of Formula 1A.

6. A pharmaceutical composition comprising:
an amount of a compound according to formula 1A,

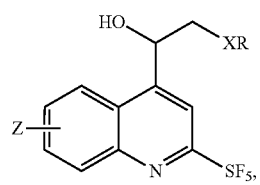

Formula 1A wherein X is O, S, —CR'R", NR',
wherein R is H, a heterocycle side chain, a straight alkyl, a cyclic alkyl, a cyclic amine, a N substituted cyclic alkyl, or a N substituted straight chain alkyl,
wherein R' and R" are each independently selected from the group consisting of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle,
wherein Z is located in positioned in positions 6-, 7-, or 8- of Formula 1A,
wherein Z is a perfluorinated or partially fluorinated alkyl; and
a pharmaceutically acceptable carrier.

7. The pharmaceutical composition of claim 6, wherein Z is selected from the group consisting of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$.

8. The pharmaceutical composition of claim 6, wherein the compound has a formula according to Formula 1

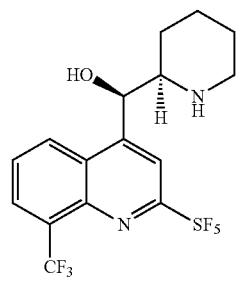

Formula 1

9. The pharmaceutical composition of claim 6, wherein the amount is an amount effective to treat or prevent infection by a protozoan of the genus *Plasmodium* in a subject in need thereof.

10. A method comprising:
administering an amount of a compound according to Formula 1A to a subject in need thereof,

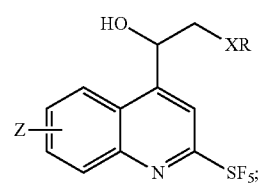

Formula 1A wherein X is O, S, —CR'R", NR',
wherein R is H, a heterocycle side chain, a straight alkyl, a cyclic alkyl, a cyclic amine, a N substituted cyclic chain alkyl, a N substituted straight chain alkyl,
wherein R' and R" are each independently selected from the group consisting of: H, a straight alkyl, a cyclic alkyl, a N substituted straight alkyl, a N substituted cyclic alkyl, a cyclic amine, a imidazole, and a triazole, or together form a cyclic amine, an aryl, or a heterocycle,
wherein Z is located in positioned in positions 6-, 7-, or 8- of Formula 1A,
wherein Z is a perfluorinated or partially fluorinated alkyl, and
wherein the subject in need thereof is infected with, suspected of being infected with, exposed to, or suspected of being exposed to a protozoan belonging to the genus *Plasmodium*.

11. The method of claim 10, wherein the amount of a compound according to Formula 1A is a therapeutically effective amount.

12. The method of claim 10, wherein the protozoan is capable of causing malaria in the subject in need thereof.

13. The method of claim 10, wherein the protozoan is resistant to chloroquine.

14. The method of claim 10, wherein the protozoan is resistant to mefloquine.

15. The method of claim 10, wherein the amount of a compound according to Formula 1A is contained in a pharmaceutical formulation further comprising a pharmaceutically acceptable carrier.

16. The method of claim 10, wherein Z is selected from the group consisting of: $CF_3$, $SF_5$, $SCF_3$, $HCF_2$, $ClCF_2$, $BrCF_2$, $ICF_2$, $HCF_2S$, $C_2F_5$, $CF_2CF_2H$, and $CF_2SF_5$.

17. The method of claim 10, wherein the compound is according to Formula 1
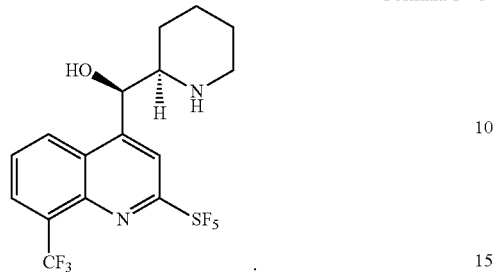
Formula 1
* * * * *